United States Patent
Delmotte et al.

(10) Patent No.: US 10,912,859 B2
(45) Date of Patent: *Feb. 9, 2021

(54) ADDITIVE ABLE TO PROVIDE UNDERWATER ADHESION

(71) Applicants: BAXTER INTERNATIONAL INC., Deerfield, IL (US); BAXTER HEALTHCARE S.A., Glattpark (CH)

(72) Inventors: Yves A. Delmotte, Neufmaison (BE); Jonathan Payssan, Uccle (FR)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 94 days.

This patent is subject to a terminal disclaimer.

(21) Appl. No.: 15/914,218

(22) Filed: Mar. 7, 2018

(65) Prior Publication Data

US 2018/0256777 A1    Sep. 13, 2018

Related U.S. Application Data

(60) Provisional application No. 62/468,574, filed on Mar. 8, 2017.

(51) Int. Cl.
| | | |
|---|---|---|
| A61L 24/04 | (2006.01) | |
| C08G 65/00 | (2006.01) | |
| A61M 5/19 | (2006.01) | |
| A61B 17/00 | (2006.01) | |
| C08G 65/333 | (2006.01) | |
| C08G 65/334 | (2006.01) | |

(52) U.S. Cl.
CPC ...... *A61L 24/046* (2013.01); *A61B 17/00491* (2013.01); *A61M 5/19* (2013.01); *C08G 65/00* (2013.01); *C08G 65/3344* (2013.01); *C08G 65/33337* (2013.01); *A61B 2017/00495* (2013.01)

(58) Field of Classification Search
CPC .................................................. A61L 24/046
See application file for complete search history.

(56) References Cited

U.S. PATENT DOCUMENTS

| | | | |
|---|---|---|---|
| 4,359,049 A | 11/1982 | Redl et al. | |
| 4,631,055 A | 12/1986 | Redl et al. | |
| 5,015,677 A | 5/1991 | Benedict et al. | |
| 5,116,315 A | 5/1992 | Capozzi et al. | |
| 5,328,955 A | 7/1994 | Rhee et al. | |
| 5,585,007 A | 12/1996 | Antanavich et al. | |
| 6,312,725 B1 | 11/2001 | Wallace et al. | |
| 6,454,786 B1 | 9/2002 | Holm et al. | |
| 6,461,325 B1 | 10/2002 | Delmotte et al. | |
| 6,534,591 B2 | 3/2003 | Rhee et al. | |
| 6,624,245 B2 | 9/2003 | Wallace et al. | |
| 6,911,496 B2 | 6/2005 | Rhee et al. | |
| 7,208,171 B2 | 4/2007 | Messersmith et al. | |
| 7,622,533 B2 | 11/2009 | Lee | |
| 7,727,547 B2 | 6/2010 | Fortune et al. | |
| 8,029,774 B2 | 10/2011 | Beckman et al. | |
| 8,067,031 B2 | 11/2011 | Daniloff et al. | |
| 8,383,092 B2 | 2/2013 | Lee et al. | |
| 8,409,602 B2 | 4/2013 | Messersmith et al. | |
| 8,460,708 B2 | 6/2013 | Daniloff et al. | |
| 8,481,073 B2 | 7/2013 | Daniloff et al. | |
| 8,512,749 B2 | 8/2013 | Sawhney et al. | |
| 8,673,286 B2 | 3/2014 | Messersmith et al. | |
| 8,791,219 B2 | 7/2014 | Grubbs et al. | |
| 8,846,849 B2 | 9/2014 | Bordoloi et al. | |
| 8,916,652 B2 | 12/2014 | Dalsin et al. | |
| 9,114,172 B2 | 8/2015 | Rhee et al. | |
| 9,115,289 B2 | 8/2015 | Lee et al. | |
| 2003/0087338 A1 | 5/2003 | Messersmith et al. | |
| 2004/0068266 A1 | 4/2004 | Delmotte | |
| 2005/0201974 A1 | 9/2005 | Schestopol et al. | |
| 2006/0071025 A1 | 4/2006 | Crews | |
| 2007/0014755 A1* | 1/2007 | Beckman | A61K 31/28 424/78.27 |
| 2009/0163845 A1 | 6/2009 | Meyer-Ingold | |
| 2012/0016390 A1 | 1/2012 | Lee et al. | |
| 2012/0116424 A1* | 5/2012 | Lee | A61L 24/046 606/151 |
| 2013/0248109 A1* | 9/2013 | Grubbs | C09J 133/26 156/325 |
| 2018/0256775 A1 | 9/2018 | Delmotte et al. | |

FOREIGN PATENT DOCUMENTS

WO    WO2015167253 A1 *  11/2015

OTHER PUBLICATIONS

Maier, G.P., Rapp. M.V., Waite, J.H., Israelachvili, J.N., & Butler, A.; Adaptive synergy between catechol and lysine promotes wet adhesion by surface salt displacement; Science; vol. 349, Issue 6248; pp. 628-632; Aug. 7, 2015.

Lin, Qi, et al.; Adhesion mechanisms of the mussel foot proteins mfp-1 and mfp-3; PNAS; vol. 104, No. 10; pp. 3782-3786; Mar. 6, 2007.

Kim, H.J., Hwang, B.H., Lim, S., Choi, B.H., Kang, S.H., & Cha, H.J.; Mussel adhesion-employed water-immiscible fluid bioadhesive for urinary fistula sealing; Biomaterials; vol. 72; pp. 104-111; Dec. 2015.

Milla, P., Dosio, F., & Cattel, L.; PEGylation of proteins and Liposomes: a Powerful and Flexible Strategy to Improve the Drug Delivery; Current Drug Metabolism; vol. 13, No. 1; pp. 105-119; 2012.

* cited by examiner

*Primary Examiner* — Michael F Pepitone
(74) *Attorney, Agent, or Firm* — K&L Gates LLP

(57) ABSTRACT

Compositions and methods for sealing tissue of a patient in a wet environment are disclosed.

22 Claims, 4 Drawing Sheets

FIG. 4A
FIG. 4B
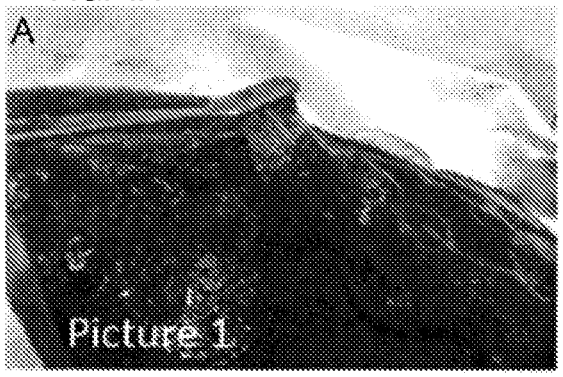
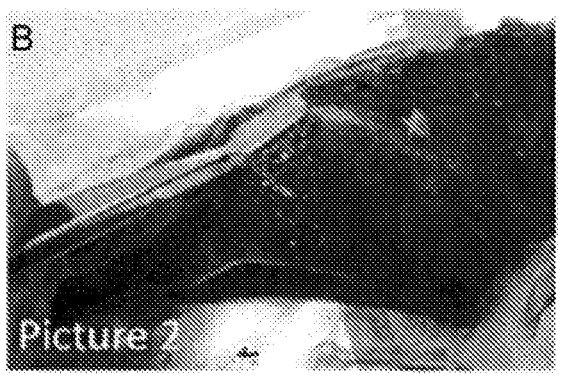
FIG. 4C
FIG. 4D
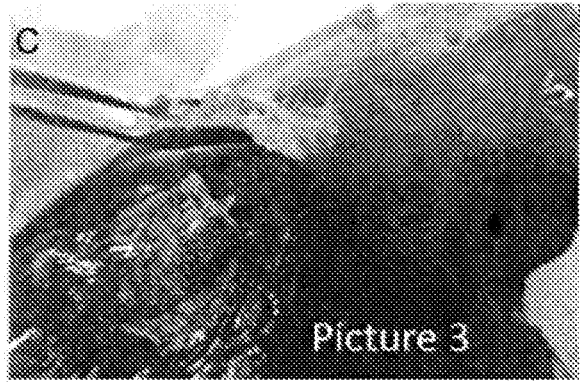
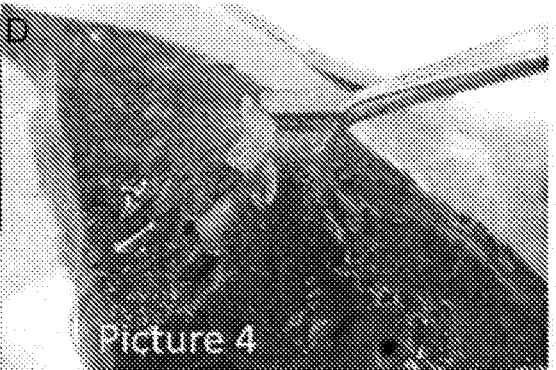

ADDITIVE ABLE TO PROVIDE UNDERWATER ADHESION

FIELD OF THE DISCLOSURE

The disclosure relates generally to an additive for surgical adhesives and sealants. More particularly, the disclosure relates to an additive for surgical adhesives and sealants to improve adhesion to wet surfaces.

BACKGROUND

Surgeons are routinely required to achieve hemostasis and stop both minor and massive bleeding, particularly of highly vascularized organs. Organs are naturally wet to facilitate their motion and reduce friction, and are further wetted during surgery due to extracorporeal fluids that are produced and use of irrigation solutions to aspirate debris, clear the field of view, and avoid adhesion formation. However, bonding to wet tissue surfaces is difficult to achieve. Current surgical adhesives and sealants often lack sufficient ability to adhere to wet surfaces.

SUMMARY

The present disclosure is directed to compositions and methods for sealing tissue of a patient under wet conditions, particularly to an additive for surgical adhesives and sealants to improve adhesion to wet surfaces.

In one aspect, the present disclosure provides a compound comprising a polymer core substituted with at least one L-3,4-dihydroxyphenylalanine (L-DOPA) group and at least one sulfhydryl-reactive group.

In one aspect, the present disclosure provides a dry powder composition comprising (i) a component having a polymer core substituted with at least two sulfhydryl groups and (ii) a component comprising a polymer core substituted with at least one L-3,4-dihydroxyphenylalanine (L-DOPA) group and at least one sulfhydryl-reactive group.

In one aspect, the present disclosure provides a solution composition comprising (i) a component having a polymer core substituted with at least two sulfhydryl groups and (ii) a component comprising a polymer core substituted with at least one L-3,4-dihydroxyphenylalanine (L-DOPA) group and at least one sulfhydryl-reactive group, wherein the solution has a pH of about 1 to about 5.5.

In one aspect, the present disclosure provides a kit comprising: (a) a dry powder composition comprising a first component having a polymer core substituted with at least two sulfhydryl groups, a second component having a polymer core substituted with at least two sulfhydryl-reactive groups, and a third component comprising a polymer core substituted with at least one L-3,4-dihydroxyphenylalanine (L-DOPA) group and at least one sulfhydryl-reactive group; (b) a first aqueous solution having a pH of about 1 to about 5.5; and (c) a second aqueous solution having a pH of about 6 to about 11; wherein each of (a), (b), and (c) is packaged separately prior to use.

In another aspect, the disclosure provides a composition prepared by reacting a component having a polymer core substituted with at least two sulfhydryl groups with (i) a component having a polymer core substituted with at least two sulfhydryl-reactive groups and (ii) a component having a polymer core substituted with at least one L-3,4-dihydroxyphenylalanine (L-DOPA) group and at least one sulfhydryl-reactive group.

In another aspect, the disclosure provides a method of sealing tissue of a patient comprising: (a) dissolving a dry powder composition comprising (i) a first component having a polymer core substituted with at least two sulfhydryl groups, (ii) a second component having a polymer core substituted with at least two sulfhydryl-reactive groups, and (iii) a third component comprising a polymer core substituted with at least one L-3,4-dihydroxyphenylalanine (L-DOPA) group and at least one sulfhydryl-reactive group in a first aqueous solution having a pH of about 1 to about 5.5 to form a homogeneous solution; (b) adding a second aqueous solution having a pH of about 6 to about 11 to the homogeneous solution to form a mixture; and (c) placing the mixture into contact with a tissue surface and allowing a three-dimensional composition to form on the tissue.

The foregoing summary is not intended to define every aspect of the disclosure, and other features and advantages of the present disclosure will become apparent from the following detailed description. The present disclosure is intended to be related as a unified document, and it should be understood that all combinations of features described herein are contemplated, even if the combination of features are not found together in the same sentence, paragraph, or section of this disclosure. In addition, the disclosure includes, as an additional aspect, all embodiments of the disclosure narrower in scope in any way than the variations specifically mentioned above. With respect to aspects of the disclosure described or claimed with "a" or "an," it should be understood that these terms mean "one or more" unless context unambiguously requires a more restricted meaning. With respect to elements described as one or more within a set, it should be understood that all combinations within the set are contemplated. If aspects of the disclosure are described as "comprising" a feature, embodiments also are contemplated "consisting of" or "consisting essentially of" the feature. Additional features and variations of the disclosure will be apparent to those skilled in the art from the entirety of this application, and all such features are intended as aspects of the disclosure.

BRIEF DESCRIPTION OF THE DRAWINGS

FIG. 4A is a photograph of Coseal DOPA (−) applied on a dry surface.

FIG. 4B is a photograph of Coseal DOPA (+) applied on a dry surface.

FIG. 4C is a photograph of Coseal DOPA (−) applied on a wet surface.

FIG. 4D is a photograph of Coseal DOPA (+) applied on a wet surface.

DETAILED DESCRIPTION

Figure 1A:
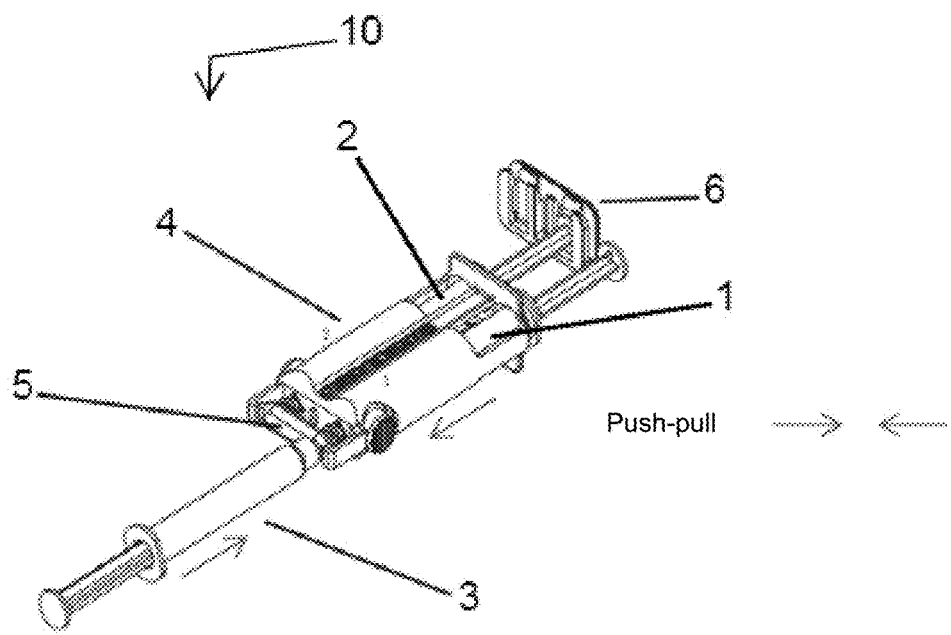
FIG. 1A shows a representative multi-compartment syringe device for generating and delivering a surgical sealant and adhesive composition according to the disclosure.

The present disclosure provides surgical adhesives and sealants suitable for application to wet surfaces. The disclosure also provides additives for surgical adhesives and sealants to improve adhesion to wet surfaces. Surgical adhesives and sealants are described, for example, in U.S. Pat. Nos. 6,312,725, 6,624,245, 6,911,496, 8,067,031, 8,460,708, and 8,481,073, which are hereby incorporated by reference in their entireties.

The surgical adhesives and sealants disclosed herein including an L-DOPA-containing additive advantageously demonstrated adhesion to both dry and wet surfaces. In particular, the surgical adhesives and sealants disclosed herein demonstrate improved adhesion to wet surfaces as compared to a surgical adhesive or sealant that does not contain L-DOPA.

Additive for Surgical Adhesives and Sealants

The disclosure provides additives for surgical adhesives and sealants to improve adhesion of the adhesives and sealants to wet surfaces. The additives have a polymer core substituted with at least one L-3,4-dihydroxyphenylalanine (L-DOPA) group and at least one electrophilic group (e.g., sulfhydryl-reactive group such as a succinimidyl group).

Suitable sulfhydryl-reactive groups include, but are not limited to, mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; isocyanates; maleimides; substituted maleimides; haloalkanes; epoxides; imines; aziridines; olefins (including conjugated olefins) such as ethenesulfonyl, etheneimino, acrylate, methacrylate, and α,β-unsaturated aldehydes and ketones; and combinations thereof.

Examples of sulfhydryl-reactive groups include, but are not limited to,

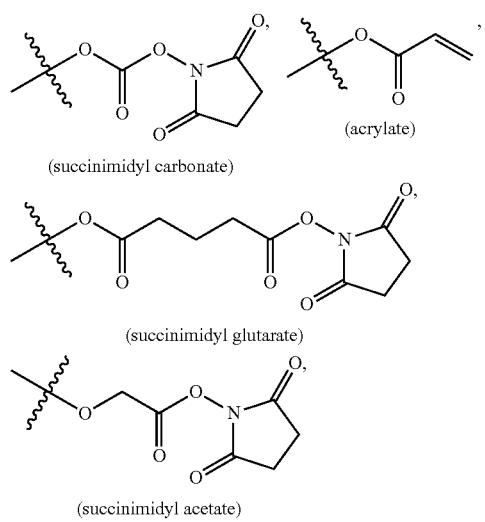

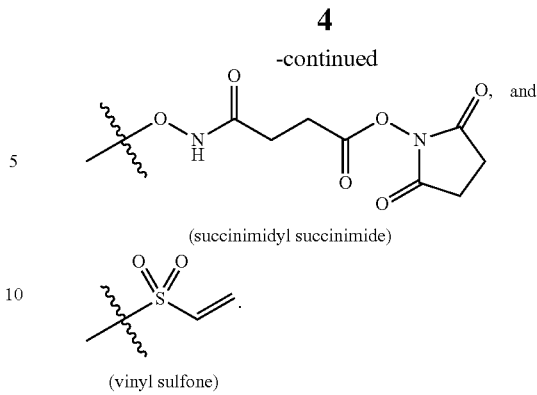

The polymer core comprises a polymer to which the L-DOPA and electrophilic groups are covalently bound. Suitable polymers include, but are not limited to, polyalkylene oxides, particularly polyethylene glycol (PEG) and poly(ethylene oxide)-poly(propylene oxide) copolymers, including block and random copolymers; polyols such as glycerol, polyglycerol (PG), particularly highly branched polyglycerol, and propylene glycol; poly(oxyalkylene)-substituted diols, and poly(oxyalkylene)-substituted polyols such as mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; poly(acrylic acids) and analogs and copolymers thereof, such as polyacrylic acid per se, polymethacrylic acid, poly(hydroxyethylmethacrylate), poly(hydroxyethylacrylate), poly(methylalkylsulfoxide methacrylates), poly(methylalkylsulfoxide acrylates) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), poly(N-isopropyl-acrylamide), and copolymers thereof; poly(olefinic alcohols) such as poly(vinyl alcohols) and copolymers thereof; poly(N-vinyl lactams) such as poly(vinyl pyrrolidones), poly(N-vinyl caprolactams), and copolymers thereof; polyoxazolines, including poly(methyloxazoline) and poly(ethyloxazoline); and polyvinylamines; as well as copolymers of any of the foregoing.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

Although a variety of different polymers can be used, as indicated above, preferred synthetic hydrophilic polymers are PEG and PG, particularly highly branched PEG. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred polymer for certain applications is a PEG having a molecular weight within the range of about 100 to about 100,000, although for highly branched PEG, far higher molecular weight polymers can be employed, up to 1,000,000 or more, providing that biodegradable sites are incorporated ensuring that all degradation products will have a molecular weight of less than about 30,000. For most PEGs, however, the preferred molecular weight is about 1,000 to about 20,000, more preferably within the range of about 7,500 to about 20,000. Most preferably, the polyethylene glycol has a molecular weight of approximately 10,000.

In an embodiment, the additive is a compound comprising a polymer core substituted with at least one L-3,4-dihydroxyphenylalanine (L-DOPA) group and at least one sulfhydryl-reactive group. In an embodiment, the polymer core of the compound is branched poly(ethylene oxide). In an embodiment, the polymer core of the compound is a 4-arm poly(ethylene oxide), a 6-arm poly(ethylene oxide), or an 8-arm poly(ethylene oxide). In an embodiment, the sulfhydryl-reactive group of the compound is a succinimidyl group, an acrylate group, or a vinyl sulfone, preferably a succinimidyl group.

In an embodiment, the additive is a compound of Formula I:

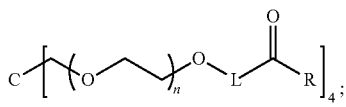
(I)

wherein each R is independently a sulfhydryl-reactive group or

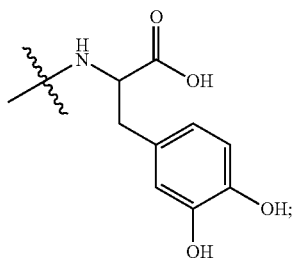 [SMILES: *NC(Cc1ccc(O)c(O)c1)C(=O)O]

L is null, —(CH$_2$)$_{1-5}$—, —CO(CH$_2$)$_{1-5}$—, or —NHCO(CH$_2$)$_{1-5}$—; and each n is independently 15 to 150; provided that at least one R group is

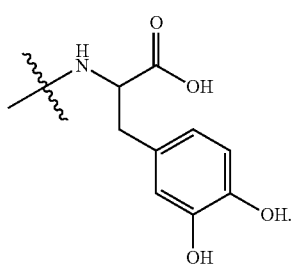

In Formula I, each of the four R groups is independently a sulfhydryl-reactive group or

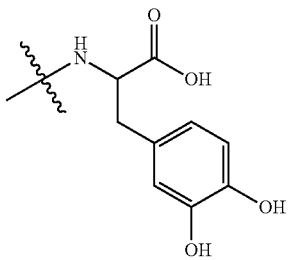 [SMILES: *NC(Cc1ccc(O)c(O)c1)C(=O)O]

and at least one R group is

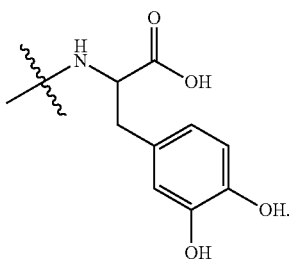 [SMILES: *NC(Cc1ccc(O)c(O)c1)C(=O)O]

In embodiments, two or three R groups are

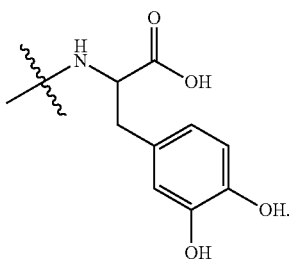 [SMILES: *NC(Cc1ccc(O)c(O)c1)C(=O)O]

In an embodiment, the sulfhydryl-reactive group is

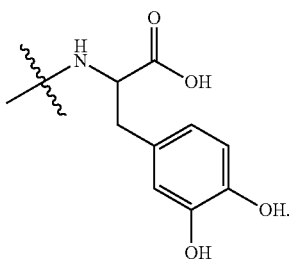

In Formula I, L is null, —(CH$_2$)$_{1-5}$—, —CO(CH$_2$)$_{1-5}$—, —NHCO(CH$_2$)$_{1-5}$—, or —(CH$_2$)$_{1-5}$NHCO(CH$_2$)$_{1-5}$—. For example, L is —CH$_2$—, —(CH$_2$)$_2$—, —(CH$_2$)$_3$—, —(CH$_2$)$_4$—, —(CH$_2$)$_5$—, —COCH$_2$—, —CO(CH$_2$)$_2$—, —CO(CH$_2$)$_3$—, —CO(CH$_2$)$_4$—, —CO(CH$_2$)$_5$—, —NHCOCH$_2$—, —NHCO(CH$_2$)$_2$—, —NHCO(CH$_2$)$_3$—, —NHCO(CH$_2$)$_4$—, —NHCO(CH$_2$)$_5$—, —CH$_2$NHCOCH$_2$—, —CH$_2$NHCO(CH$_2$)$_2$—, —CH$_2$NHCO(CH$_2$)$_3$—, —CH$_2$NHCO(CH$_2$)$_4$—, —CH$_2$NHCO(CH$_2$)$_5$—, —(CH$_2$)$_2$NHCOCH$_2$—, —(CH$_2$)$_2$NHCO(CH$_2$)$_2$—, —(CH$_2$)$_2$NHCO(CH$_2$)$_3$—, —(CH$_2$)$_2$NHCO(CH$_2$)$_4$—, —(CH$_2$)$_2$NHCO(CH$_2$)$_5$—, —(CH$_2$)$_3$NHCOCH$_2$—, —(CH$_2$)$_3$NHCO(CH$_2$)$_2$—, —(CH$_2$)$_3$NHCO —(CH$_2$)$_3$—, —(CH$_2$)$_3$NHCO(CH$_2$)$_4$—, —(CH$_2$)$_3$ NHCO (CH$_2$)$_5$—, —(CH$_2$)$_4$NHCOCH$_2$—, —(CH$_2$)$_4$ NHCO (CH$_2$)$_2$—, —(CH$_2$)$_4$NHCO(CH$_2$)$_3$—, —(CH$_2$)$_4$ NHCO (CH$_2$)$_4$—, —(CH$_2$)$_4$NHCO(CH$_2$)$_5$—, —(CH$_2$)$_5$ NHCOCH$_2$—, —(CH$_2$)$_5$NHCO(CH$_2$)$_2$—, —(CH$_2$)$_5$ NHCO (CH$_2$)$_3$—, —(CH$_2$)$_5$NHCO(CH$_2$)$_4$—, —(CH$_2$)$_5$ NHCO (CH$_2$)$_5$—. In an embodiment, L is —CO(CH$_2$)$_3$— or —NHCO(CH$_2$)$_2$—.

In Formula I, each n is independently 15 to 150, for example, 30 to 100, 35 to 90, 40 to 80, 45 to 70, 50 to 60, 54 to 58, 20 to 40, 40 to 60, 50 to 80, and/or 80 to 130.

In Formula I, suitable -LCOR include, but are not limited to,

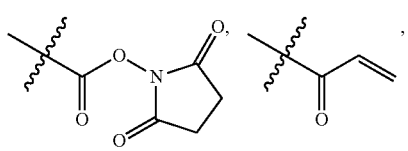

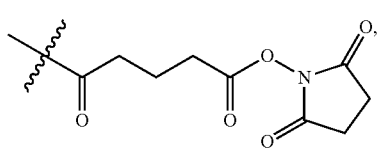

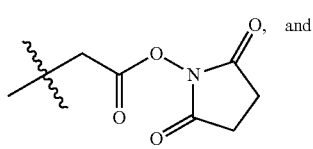

In an embodiment, Formula I has a structure:

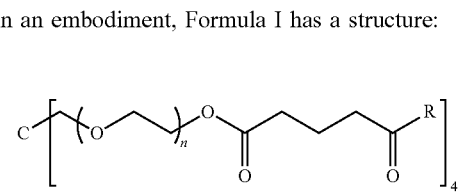

wherein each n is independently 15 to 150, for example, 30 to 100, 35 to 90, 40 to 80, 45 to 70, 50 to 60, 54 to 58, 20 to 40, 40 to 60, 50 to 80, and/or 80 to 130; and
each R is independently a sulfhydryl-reactive group

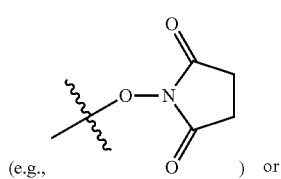

(e.g., ) or

-continued

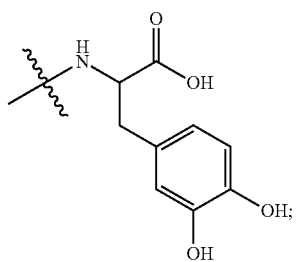

wherein at least one R group (e.g., 1, 2, or 3 R groups) is/are

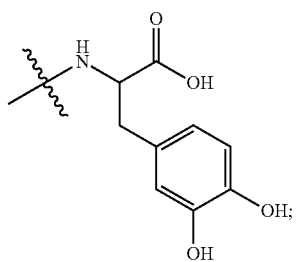

In an embodiment, the additive is a compound of Formula II or Formula III:

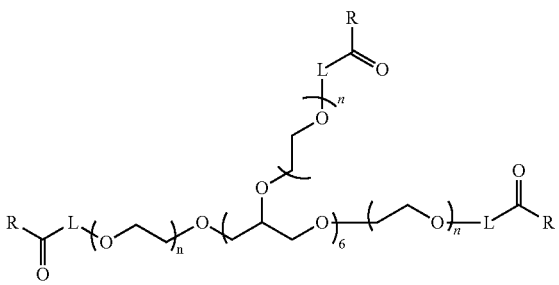

(II)

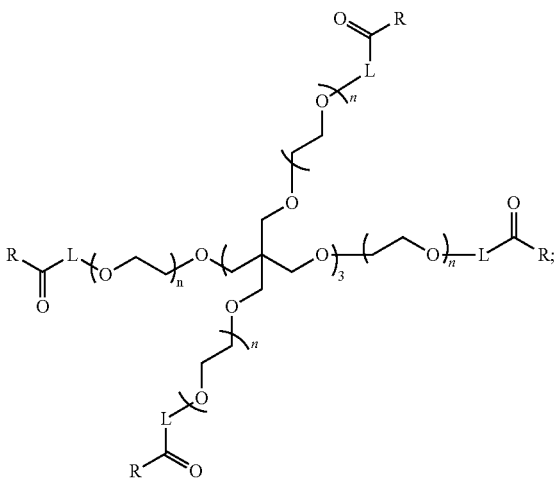

(III)

wherein each R is independently a sulfhydryl-reactive group or

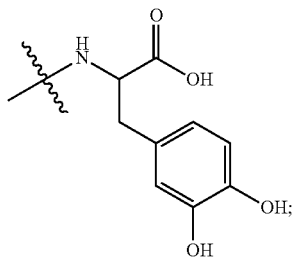 [SMILES: *NC(Cc1ccc(O)c(O)c1)C(=O)O]

L is null, —(CH$_2$)$_{1-5}$—, —CO(CH$_2$)$_{1-5}$—, —NHCO(CH$_2$)$_{1-5}$—, or —(CH$_2$)$_{15}$NHCO(CH$_2$)$_{1-5}$—; and each n is independently 15 to 150; provided that at least one R group is

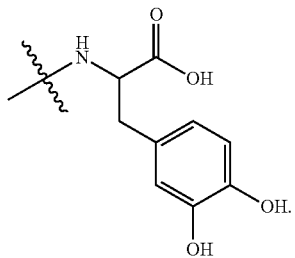 [SMILES: *NC(Cc1ccc(O)c(O)c1)C(=O)O]

In Formula II and Formula III, each of the eight R groups is independently a sulfhydryl-reactive group or

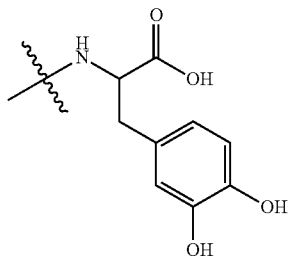 [SMILES: *NC(Cc1ccc(O)c(O)c1)C(=O)O]

and at least one R group is

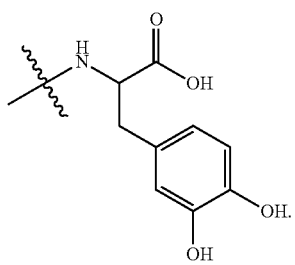 [SMILES: *NC(Cc1ccc(O)c(O)c1)C(=O)O]

In embodiments, two, three, four, five, six, or seven R groups are

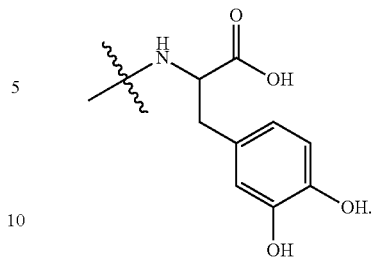

In an embodiment, the sulfhydryl-reactive group is

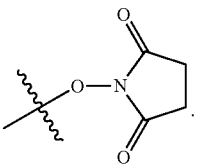 [SMILES: *ON1C(=O)CCC1=O]

In Formula II and Formula III, L is null, —(CH$_2$)$_{1-5}$—, —CO(CH$_2$)$_{1-5}$—, —NHCO(CH$_2$)$_{1-5}$—, or —(CH$_2$)$_{1-5}$NHCO(CH$_2$)$_{1-5}$—. For example, L is —CH$_2$—, —(CH$_2$)$_2$—, —(CH$_2$)$_3$—, —(CH$_2$)$_4$—, —(CH$_2$)$_5$—, —COCH$_2$—, —CO(CH$_2$)$_2$—, —CO(CH$_2$)$_3$—, —CO(CH$_2$)$_4$—, —CO(CH$_2$)$_5$—, —NHCOCH$_2$—, —NHCO(CH$_2$)$_2$—, —NHCO(CH$_2$)$_3$—, —NHCO(CH$_2$)$_4$—, —NHCO(CH$_2$)$_5$—, —CH$_2$NHCOCH$_2$—, —CH$_2$NHCO(CH$_2$)$_2$—, —CH$_2$NHCO(CH$_2$)$_3$—, —CH$_2$NHCO(CH$_2$)$_4$—, —CH$_2$NHCO(CH$_2$)$_5$—, —(CH$_2$)$_2$NHCOCH$_2$—, —(CH$_2$)$_2$NHCO(CH$_2$)$_2$—, —(CH$_2$)$_2$NHCO(CH$_2$)$_3$—, —(CH$_2$)$_2$NHCO(CH$_2$)$_4$—, —(CH$_2$)$_2$NHCO(CH$_2$)$_5$—, —(CH$_2$)$_3$NHCOCH$_2$—, —(CH$_2$)$_3$NHCO(CH$_2$)$_2$—, —(CH$_2$)$_3$NHCO(CH$_2$)$_3$—, —(CH$_2$)$_3$NHCO(CH$_2$)$_4$—, —(CH$_2$)$_3$NHCO(CH$_2$)$_5$—, —(CH$_2$)$_4$NHCOCH$_2$—, —(CH$_2$)$_4$NHCO(CH$_2$)$_2$—, —(CH$_2$)$_4$NHCO(CH$_2$)$_3$—, —(CH$_2$)$_4$NHCO(CH$_2$)$_4$—, —(CH$_2$)$_4$NHCO(CH$_2$)$_5$—, —(CH$_2$)$_5$NHCOCH$_2$—, —(CH$_2$)$_5$NHCO(CH$_2$)$_2$—, —(CH$_2$)$_5$NHCO(CH$_2$)$_3$—, —(CH$_2$)$_5$NHCO(CH$_2$)$_4$—, —(CH$_2$)$_5$NHCO(CH$_2$)$_5$—. In an embodiment, L is —CO(CH$_2$)$_2$—, —CO(CH$_2$)$_3$—, or —(CH$_2$)$_2$NHCO(CH$_2$)$_2$—.

In Formula II and Formula III, each n is independently 15 to 150, for example, 20 to 40, 40 to 60, 50 to 80, and/or 80 to 130.

In Formula II and Formula III, suitable -LCOR include, but are not limited to,

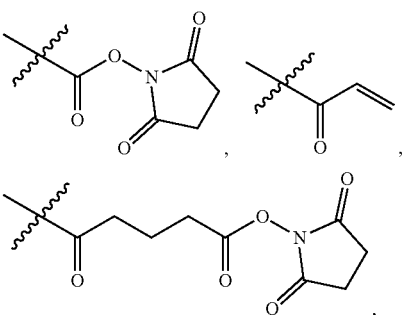

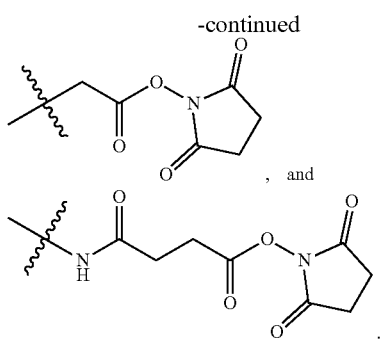
, and

Dry Powder Composition

The present disclosure provides a dry powder composition that contains at least three biocompatible, non-immunogenic components having reactive groups thereon, with the functional groups selected so as to enable reaction between the components, i.e., crosslinking, to form a three-dimensional matrix. Each component has a polymer core substituted with reactive groups. The dry powder composition contains a first component having a polymer core substituted with nucleophilic groups (e.g., amino groups or thiol groups), a second component having a polymer core substituted with electrophilic groups (e.g., succinimidyl groups), and a third component having a polymer core substituted with at least one L-3,4-dihydroxyphenylalanine (L-DOPA) group and at least one electrophilic group (e.g., a succinimidyl group) as shown, for example, in Formula I, II, or III above. Dry powder compositions having more than three components also are encompassed, where additional components may have nucleophilic or electrophilic groups.

The reactive groups are selected so that the components are essentially non-reactive in a dry environment, for example, when the component having a polymer core substituted with nucleophilic groups, the component having a polymer core substituted with electrophilic groups, and the component having a polymer core substituted with an L-DOPA group and an electrophilic groups are formulated as and/or provided as a homogeneous dry powder. Upon exposure to an aqueous environment, the components are rendered reactive and a plurality of components are then able to react in the aqueous environment to form a three-dimensional matrix. This matrix is preferably formed without input of any external energy, for example, at room temperature or at slightly elevated temperature.

The composition is particularly suitable for application involving contact between a biological system and the composition and/or the three-dimensional matrix formed therefrom. The biological system can be a biological tissue, and in a preferred embodiment, is living tissue.

The resulting three-dimensional matrix is useful in a variety of contexts, and is particularly useful as a biomaterial for medical applications, such as for bioadhesion, tissue augmentation, tissue sealing, vascular sealing, needle hole sealing, hemostasis, and the prevention of adhesions following a surgical procedure or injury, for example.

In one embodiment, substantially immediately or immediately upon exposure to the aqueous environment, the reactive groups on the components of the composition begin to react and form a three-dimensional matrix. The term "substantially immediately" is intended to mean within less than five minutes, preferably within less than two minutes, and the term "immediately" is intended to mean within less than one minute, preferably within less than 30 seconds.

Typically, the three-dimensional composition will be completely formed within about 30 minutes.

The homogeneous dry powder composition is comprised of: a first component having a polymeric core substituted with nucleophilic groups (e.g., amino groups or thiol groups), a second component having a polymeric core substituted with electrophilic groups (e.g., succinimidyl groups), and a third component having a polymer core substituted with at least one L-3,4-dihydroxyphenylalanine (L-DOPA) group and at least one electrophilic group (e.g., a succinimidyl group). The nucleophilic and electrophilic groups are non-reactive with one another when the first, second, and third components are admixed in a dry environment but are rendered reactive upon exposure to an aqueous environment such that the components react in the aqueous environment to form a three-dimensional matrix. In some cases, the nucleophilic and electrophilic groups are relatively non-reactive with one another in an aqueous environment having an acidic pH, but are rendered reactive upon exposure to an aqueous environment having a basic pH. In order for a three-dimensional matrix to be formed, there is a plurality of reactive groups present in each of the first and second components, and optionally the third component. In a preferred embodiment, the first component has a polymeric core substituted with two or more (e.g., 3, 4, 5, 6, 7, or 8) nucleophilic groups, and the second component has a polymeric core substituted with two or more (e.g., 3, 4, 5, 6, 7, or 8) electrophilic groups.

The selection of electrophilic groups provided on the second and third components is made so that reaction is possible with the specific nucleophilic groups on the first component. Thus, when the nucleophilic groups are sulfhydryl moieties, the electrophilic groups are selected so as to react with sulfhydryl moieties. Suitable sulfhydryl-reactive groups include, but are not limited to, mixed anhydrides; ester derivatives of phosphorus; ester derivatives of p-nitrophenol, p-nitrothiophenol and pentafluorophenol; esters of substituted hydroxylamines, including N-hydroxyphthalimide esters, N-hydroxysuccinimide esters, N-hydroxysulfosuccinimide esters, and N-hydroxyglutarimide esters; esters of 1-hydroxybenzotriazole; 3-hydroxy-3,4-dihydro-benzotriazin-4-one; 3-hydroxy-3,4-dihydro-quinazoline-4-one; carbonylimidazole derivatives; acid chlorides; ketenes; isocyanates; maleimides; substituted maleimides; haloalkanes; epoxides; imines; aziridines; olefins (including conjugated olefins) such as ethenesulfonyl, etheneimino, acrylate, methacrylate, and α,β-unsaturated aldehydes and ketones; and combinations thereof.

Examples of sulfhydryl-reactive groups include, but are not limited to,

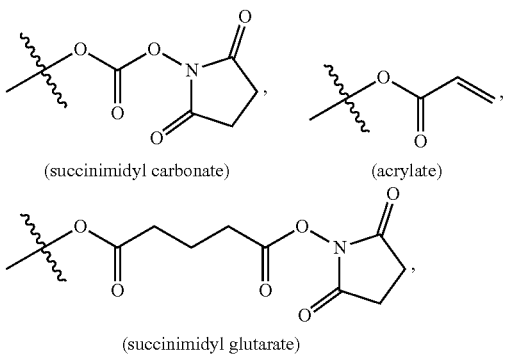

(succinimidyl carbonate)  (acrylate)

(succinimidyl glutarate)

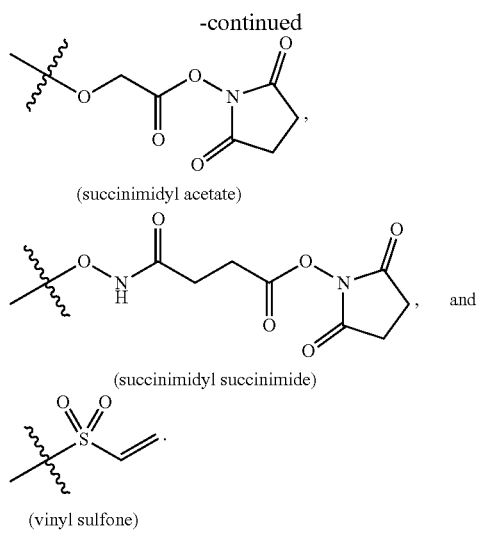

(succinimidyl acetate)

(succinimidyl succinimide), and (vinyl sulfone)

The polymer core of each component comprises a polymer to which the reactive groups are bound. Suitable polymers include, but are not limited to, polyalkylene oxides, particularly polyethylene glycol (PEG) and poly(ethylene oxide)-poly(propylene oxide) copolymers, including block and random copolymers; polyols such as glycerol, polyglycerol (PG), particularly highly branched polyglycerol, and propylene glycol; poly(oxyalkylene)-substituted diols, and poly(oxyalkylene)-substituted polyols such as mono-, di- and tri-polyoxyethylated glycerol, mono- and di-polyoxyethylated propylene glycol, and mono- and di-polyoxyethylated trimethylene glycol; polyoxyethylated sorbitol, polyoxyethylated glucose; poly(acrylic acids) and analogs and copolymers thereof, such as polyacrylic acid per se, polymethacrylic acid, poly(hydroxyethylmethacrylate), poly(hydroxyethylacrylate), poly(methylalkylsulfoxide methacrylates), poly(methylalkylsulfoxide acrylates) and copolymers of any of the foregoing, and/or with additional acrylate species such as aminoethyl acrylate and mono-2-(acryloxy)-ethyl succinate; polymaleic acid; poly(acrylamides) such as polyacrylamide per se, poly(methacrylamide), poly(dimethylacrylamide), poly(N-isopropyl-acrylamide), and copolymers thereof; poly(olefinic alcohols) such as poly(vinyl alcohols) and copolymers thereof; poly(N-vinyl lactams) such as poly(vinyl pyrrolidones), poly(N-vinyl caprolactams), and copolymers thereof; polyoxazolines, including poly(methyloxazoline) and poly(ethyloxazoline); and polyvinylamines; as well as copolymers of any of the foregoing.

Those of ordinary skill in the art will appreciate that synthetic polymers such as polyethylene glycol cannot be prepared practically to have exact molecular weights, and that the term "molecular weight" as used herein refers to the weight average molecular weight of a number of molecules in any given sample, as commonly used in the art. Thus, a sample of PEG 2,000 might contain a statistical mixture of polymer molecules ranging in weight from, for example, 1,500 to 2,500 daltons with one molecule differing slightly from the next over a range. Specification of a range of molecular weights indicates that the average molecular weight may be any value between the limits specified, and may include molecules outside those limits. Thus, a molecular weight range of about 800 to about 20,000 indicates an average molecular weight of at least about 800, ranging up to about 20 kDa.

Although a variety of different polymers can be used in the present compositions, as indicated above, preferred synthetic hydrophilic polymers are PEG and PG, particularly highly branched PEG. Various forms of PEG are extensively used in the modification of biologically active molecules because PEG lacks toxicity, antigenicity, and immunogenicity (i.e., is biocompatible), can be formulated so as to have a wide range of solubilities, and does not typically interfere with the enzymatic activities and/or conformations of peptides. A particularly preferred polymer for certain applications is a PEG having a molecular weight within the range of about 100 to about 100,000, although for highly branched PEG, far higher molecular weight polymers can be employed, up to 1,000,000 or more, providing that biodegradable sites are incorporated ensuring that all degradation products will have a molecular weight of less than about 30,000. For most PEGs, however, the preferred molecular weight is about 1,000 to about 20,000, more preferably within the range of about 7,500 to about 20,000. Most preferably, the polyethylene glycol has a molecular weight of approximately 10,000.

Multi-functionalized forms of PEG are of particular interest and include, but are not limited to, PEG succinimidyl glutarate, PEG succinimidyl propionate, PEG succinimidyl butylate, PEG succinimidyl acetate, PEG succinimidyl succinamide, PEG succinimidyl carbonate, PEG propionaldehyde, PEG glycidyl ether, PEG-isocyanate, and PEG-vinylsulfone. Many such forms of PEG are described in U.S. Pat. Nos. 5,328,955 and 6,534,591, which are hereby incorporated by reference in their entireties. Various forms of multi-amino PEG are commercially available from sources such as PEG Shop, a division of SunBio of South Korea (www.sunbio.com), Nippon Oil and Fats (Yebisu Garden Place Tower, 20-3 Ebisu 4-chome, Shibuya-ku, Tokyo), Nektar Therapeutics (San Carlos, Calif., formerly Shearwater Polymers, Huntsville, Ala.) and from Huntsman's Performance Chemicals Group (Houston, Tex.) under the name Jeffamine® polyoxyalkyleneamines. Multi-amino PEGs include the Jeffamine® diamines ("D" series) and triamines ("T" series), which contain two and three primary amino groups per molecule. Poly(sulfhydryl) PEGs are available from Nektar Therapeutics, e.g., in the form of pentaerythritol poly(ethylene glycol) ether tetra-sulfhydryl (molecular weight 10,000). Various forms of multi-arm (e.g., 4-, 6-, and 8-arm) PEG also are commercially available from sources such as Creative PEGWorks (Chapel Hill, N.C.) and Sigma-Aldrich (St. Louis, Mo.).

In an embodiment, the first component polymer core, second component polymer core, and third component polymer core are all branched poly(ethylene oxide). In an embodiment, the first component polymer core, second component polymer core, and third component polymer core are all 4-arm poly(ethylene oxide). In an embodiment, the first component polymer core, second component polymer core, and third component polymer core are all 8-arm poly(ethylene oxide). In an embodiment, the first component polymer core, second component polymer core, and third component polymer core are independently 4-arm poly(ethylene oxide) and/or 8-arm poly(ethylene oxide). In embodiments, the second and/or third component sulfhydryl-reactive group is a succinimidyl group, an acrylate group, or a vinyl sulfone, preferably a succinimidyl group. In an embodiment, the first component comprises a 4-arm, thiol-terminated poly(ethylene oxide) and the second component comprises a 4-arm, succinimidyl-terminated poly(ethylene oxide). In an embodiment, the dry powder composition comprises an 8-arm, succinimidyl-terminated poly (ethylene oxide) and an 8-arm, thiol-terminated poly(ethylene oxide). In an embodiment, the dry powder composition comprises an 8-arm, succinimidyl-terminated poly(ethylene oxide) and a 4-arm, thiol-terminated poly(ethylene oxide). In an embodiment, the dry powder composition comprises a 4-arm, succinimidyl-terminated poly(ethylene oxide) and an 8-arm, thiol-terminated poly(ethylene oxide).

In an embodiment, the first component is

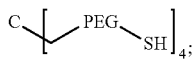

wherein PEG is poly(ethylene oxide). Each PEG independently includes a number of ethylene oxide units, for example, 15 to 150, 30 to 100, 35 to 90, 40 to 80, 45 to 70, 50 to 60, 54 to 58, 20 to 40, 40 to 60, 50 to 80, and/or 80 to 130 ethylene oxide units.

In an embodiment, the second component is

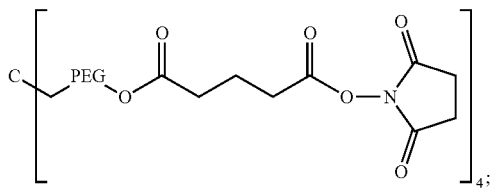

wherein PEG is poly(ethylene oxide). Each PEG independently includes a number of ethylene oxide units, for example, 15 to 150, 30 to 100, 35 to 90, 40 to 80, 45 to 70, 50 to 60, 54 to 58, 20 to 40, 40 to 60, 50 to 80, and/or 80 to 130 ethylene oxide units.

In an embodiment, the third component has a structure of Formula I, Formula II, or Formula III as described herein.

In an embodiment, the 4-arm, succinimidyl-terminated poly(ethylene oxide) has a weight average molecular weight ($M_w$) of about 8 kDa to about 14 kDa, such as about 9 kDa to about 13 kDa, about 10 kDa to about 12 kDa, and/or about 11 kDa. In an embodiment, the 4-arm, thiol-terminated poly(ethylene oxide) has a weight average molecular weight ($M_w$) of about 7 kDa to about 13 kDa, such as about 8 kDa to about 12 kDa, 9 kDa to about 11 kDa, and/or about 10 kDa. In an embodiment, the third component has a weight average molecular weight ($M_w$) of about 8 kDa to about 14 kDa, such as about 9 kDa to about 13 kDa, about 10 kDa to about 12 kDa, and/or about 11 kDa.

In one aspect, the disclosure provides a dry powder composition comprising (i) a component having a polymer core substituted with at least two (e.g., 3, 4, 5, 6, 7, or 8) sulfhydryl groups, for example, as described above, and (ii) a component comprising a polymer core substituted with at least one (e.g., 2, 3, 4, 5, 6, or 7) L-3,4-dihydroxyphenylalanine (L-DOPA) group and at least one (e.g., 2, 3, 4, 5, 6, or 7) sulfhydryl-reactive group, as shown, for example, in Formula I, Formula II, or Formula III above. In an embodiment, the dry powder composition further comprises a component having a polymer core substituted with at least two (e.g., 3, 4, 5, 6, 7, or 8) sulfhydryl-reactive groups, for example, as described above.

Formation of the Three-Dimensional Matrix

A three-dimensional matrix is formed by: (a) providing (i) a first component having a polymeric core substituted with nucleophilic groups (e.g., amino groups or thiol groups), (ii) a second component having a polymeric core substituted with electrophilic groups (e.g., succinimidyl groups), and (iii) a third component comprising a polymer core substituted with at least one L-3,4-dihydroxyphenylalanine (L-DOPA) group and at least one electrophilic group (e.g., a succinimidyl group); (b) rendering the nucleophilic and electrophilic groups reactive by exposing the first component, second component, and third component to an aqueous environment having a pH sufficient to effect reaction; and (c) allowing a three-dimensional matrix to form. Typically, the matrix is formed, e.g., by polymerization, without input of any external energy.

In one embodiment, a three-dimensional matrix is formed by: (a) dissolving a dry powder composition comprising (i) a first component having a polymer core substituted with at least two sulfhydryl groups, (ii) a second component having a polymer core substituted with at least two sulfhydryl-reactive groups, and (iii) a third component comprising a polymer core substituted with at least one L-3,4-dihydroxyphenylalanine (L-DOPA) group and at least one sulfhydryl-reactive group in a first aqueous solution having a pH of about 1 to about 5.5 to form a homogeneous solution; (b) adding a second aqueous solution having a pH of about 6 to about 11 to the homogeneous solution to form a mixture; and (c) placing the mixture into contact with a tissue surface and allowing a three-dimensional composition to form on the tissue surface.

The first, second, and third components of the dry powder composition are typically combined in amounts such that the number of nucleophilic groups (e.g., amino groups or thiol groups) in the mixture is approximately equal to the number of electrophilic groups (e.g., succinimidyl groups) in the mixture. As used in this context, the term "approximately" refers to a 2:1 to 1:2 ratio of moles of nucleophilic groups to moles of electrophilic groups. A 1:1 molar ratio of nucleophilic to electrophilic groups is generally preferred.

The first, second, and third components are blended together to form a homogeneous dry powder. This powder is then combined with an aqueous solution having a pH within the range of about 1.0 to 5.5, such as about 1.2 to about 5, about 1.4 to about 4.5, about 1.5 to about 4, about 1.6 to about 3.5, about 1.7 to about 3, about 1.8 to about 2.7, about 1.9 to about 2.5, about 2 to about 2.4, and/or about 2.1 to about 2.3, to form a homogeneous acidic aqueous solution, and this solution is then combined with an aqueous solution having a pH within the range of about 6.0 to 11.0, such as about 7 to about 10.5, such as about 8 to about 10, about 9 to about 10, about 9.3 to about 10, about 9.5 to about 9.9, about 9.6 to about 9.8, about 9.65 to about 9.75, and/or about 9.7, to form a reactive solution.

The acidic aqueous solutions having a pH within the range of about 1.0 to 5.5, include by way of illustration and not limitation, solutions of: citric acid, hydrochloric acid, phosphoric acid, sulfuric acid, 3-[(1,1-dimethyl-2-hydroxyethyl)amino]-2-hydroxypropanesulfonic acid (AMPSO), acetic acid, lactic acid, and combinations thereof. In a preferred embodiment, the acidic aqueous solution is a solution of citric acid, hydrochloric acid, phosphoric acid, sulfuric acid, and combinations thereof.

Regardless of the precise acidifying agent, the acidic solution preferably has a pH such that it retards the reactivity of the nucleophilic groups on the first component. For example, a pH of 2.1 is generally sufficient to retard the nucleophilicity of thiol groups. An exemplary acidic solution is a solution of hydrochloric acid, having a concentration of about 6.3 mM and a pH in the range of 2.1 to 2.3. This solution may be prepared by combining concentrated hydrochloric acid with water, i.e., by diluting concentrated hydrochloric acid with water.

In one aspect, the disclosure provides a solution composition comprising (i) a component having a polymer core substituted with at least two (e.g., 3, 4, 5, 6, 7, or 8) sulfhydryl groups, for example, as described above, and (ii) a component comprising a polymer core substituted with at least one (e.g., 2, 3, 4, 5, 6, or 7) L-3,4-dihydroxyphenylalanine (L-DOPA) group and at least one (e.g., 2, 3, 4, 5, 6, or 7) sulfhydryl-reactive group, as shown, for example, in Formula I, Formula II, or Formula III above, wherein the solution has a pH of about 1 to about 5.5. In an embodiment, the solution composition further comprises a component having a polymer core substituted with at least two (e.g., 3, 4, 5, 6, 7, or 8) sulfhydryl-reactive groups, for example, as described above.

Basic aqueous solutions having a pH within the range of about 6.0 to 11.0, include by way of illustration and not limitation, solutions of: glutamate, acetate, carbonate and carbonate salts (e.g., sodium carbonate, sodium carbonate monohydrate and sodium bicarbonate), borate, phosphate and phosphate salts (e.g., monobasic sodium phosphate monohydrate and dibasic sodium phosphate), and combinations thereof. In a preferred embodiment, the basic aqueous solution is a solution of carbonate salts, phosphate salts, and combinations thereof.

In general, the basic solution is an aqueous solution that neutralizes the effect of the acidic solution, when it is added to the homogeneous solution of the first and second components and the acid solution, so that the nucleophilic groups of the first component regain their nucleophilic character (that has been masked by the action of the acidic solution), thus allowing the nucleophilic groups to react with the electrophilic groups of the second component. An exemplary basic solution is an aqueous solution of carbonate and phosphate salts, e.g., sodium phosphate and sodium carbonate.

In an embodiment, the three-dimensional matrix comprises a crosslinked polymeric material having a structure:

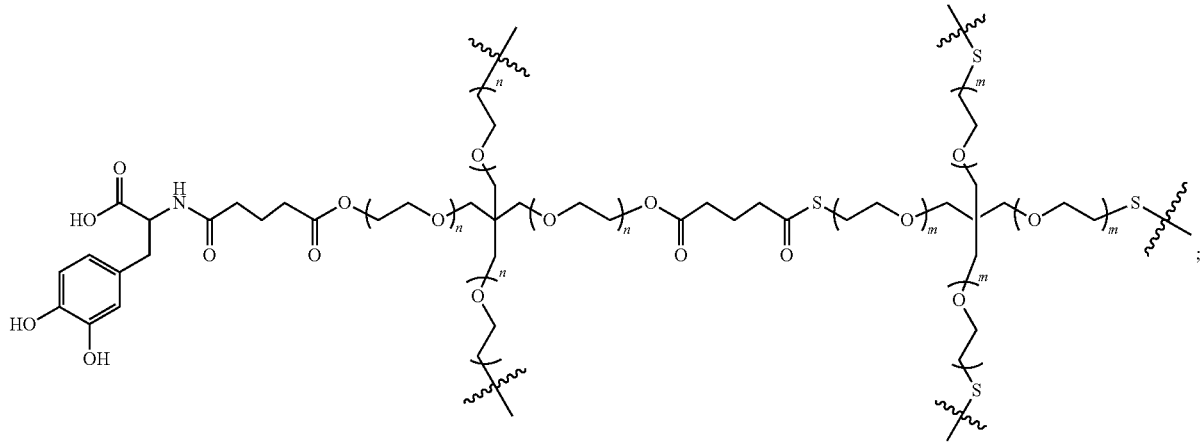

wherein each n is independently 15 to 150, 30 to 100, 35 to 90, 40 to 80, 45 to 70, 50 to 60, 54 to 58, 20 to 40, 40 to 60, 50 to 80, and/or 80 to 130; and each m is independently 15 to 150, 30 to 100, 35 to 90, 40 to 80, 45 to 70, 50 to 60, 54 to 58, 20 to 40, 40 to 60, 50 to 80, and/or 80 to 130. In the formula above, use of the symbol ∿ indicates that the molecular structure beyond this point is unspecified crosslinked material generally formed by reaction of the first component, the second component, and L-DOPA as described herein. The formula above is a representative example of a structure generally formed by reaction of a 4-arm, sulfhydryl-reactive group-terminated poly(ethylene oxide), a 4-arm, thiol-terminated poly(ethylene oxide), and L-DOPA as described herein.

In an embodiment, the three-dimensional matrix comprises a crosslinked polymeric material having a structure:

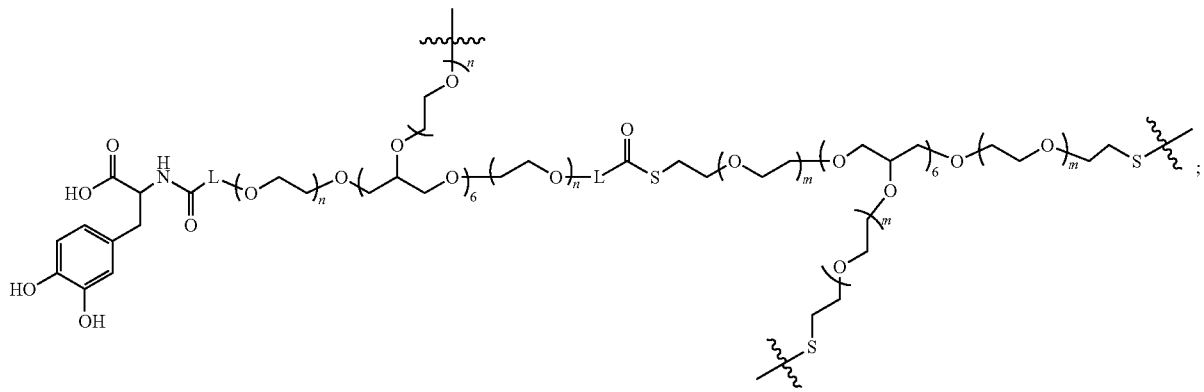

wherein L is null, —$(CH_2)_{1-5}$—, —$CO(CH_2)_{1-5}$—, —$NHCO(CH_2)_{1-5}$—, or —$(CH_2)_{1-5}NHCO(CH_2)_{1-5}$—; each n is independently 15 to 150, 20 to 40, 40 to 60, 50 to 80, and/or 80 to 130; and each m is independently 15 to 150, 20 to 40, 40 to 60, 50 to 80, and/or 80 to 130. In the formula above, use of the symbol ∿ indicates that the molecular structure beyond this point is unspecified crosslinked material generally formed by reaction of the first component, the second component, and L-DOPA as described herein. The formula above is a representative example of a structure generally formed by reaction of an 8-arm, sulfhydryl-reactive group-terminated poly(ethylene oxide), an 8-arm, thiol-terminated poly(ethylene oxide), and L-DOPA as described herein.

In an embodiment, the three-dimensional matrix comprises a crosslinked polymeric material having a structure:

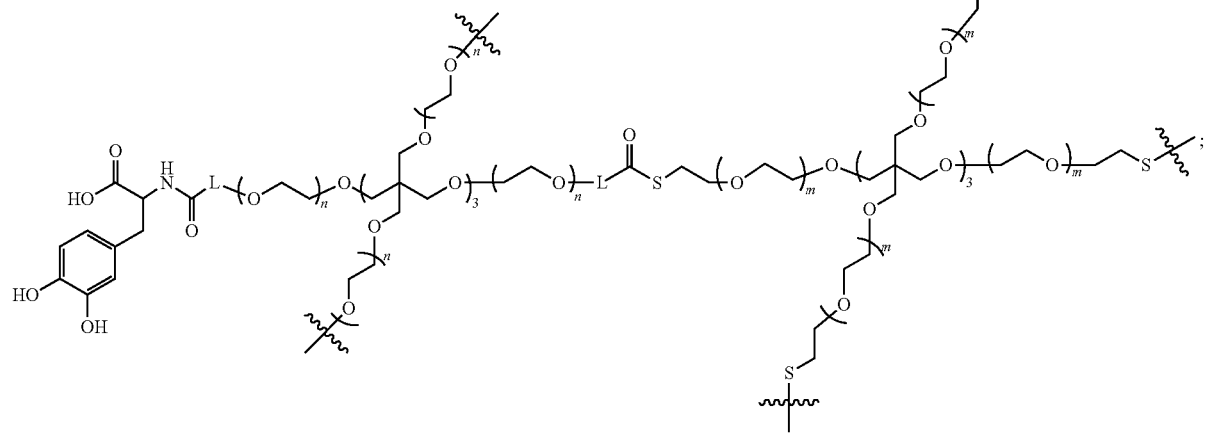

wherein L is null, —$(CH_2)_{1-5}$—, —$CO(CH_2)_{1-5}$—, —$NHCO(CH_2)_{1-5}$—, or —$(CH_2)_{1-5}NHCO(CH_2)_{1-5}$—; each n is independently 15 to 150, 20 to 40, 40 to 60, 50 to 80, and/or 80 to 130; and each m is independently 15 to 150, 20 to 40, 40 to 60, 50 to 80, and/or 80 to 130. In the formula above, use of the symbol ∿ indicates that the molecular structure beyond this point is unspecified crosslinked material generally formed by reaction of the first component, the second component, and L-DOPA as described herein. The formula above is a representative example of a structure generally formed by reaction of an 8-arm, sulfhydryl-reactive group-terminated poly(ethylene oxide), an 8-arm, thiol-terminated poly(ethylene oxide), and L-DOPA as described herein.

In an embodiment, the three-dimensional matrix is prepared by reacting a component having a polymer core substituted with at least two (e.g., 3, 4, 5, 6, 7, or 8) sulfhydryl groups with (i) a component having a polymer core substituted with at least two (e.g., 3, 4, 5, 6, 7, or 8) sulfhydryl-reactive groups and (ii) a component having a polymer core substituted with at least one (e.g., 2, 3, 4, 5, 6, or 7) L-3,4-dihydroxyphenylalanine (L-DOPA) group and at least one (e.g., 2, 3, 4, 5, 6, or 7) sulfhydryl-reactive group.

Delivery Systems

Multi-Compartment Devices: Suitable delivery systems for the homogeneous dry powder composition and the two aqueous solutions may involve a multi-compartment device, where one or more compartments contain the powder and one or more compartments contain the aqueous solutions needed to provide for the aqueous environment, such that the dry powder composition can be exposed to the aqueous environment as it leaves its respective compartment. Many devices that are adapted for delivery of multi-component tissue sealants/hemostatic agents are well known in the art and can also be used. Alternatively, the dry powder composition can be delivered using any type of controllable extrusion system, or it can be delivered manually in the form of a dry powder, and exposed to the aqueous environment at the site of administration.

The homogeneous dry powder composition and the two aqueous solutions may be conveniently formed under aseptic conditions by placing each of the three ingredients (dry powder, acidic solution and basic solution) into separate syringe barrels. For example, the dry powder composition, first aqueous solution and second aqueous solution can be housed separately in a multiple-compartment syringe system having multiple syringe barrels, a mixing head, and an exit orifice. The first aqueous solution can be added to the syringe barrel housing the dry powder composition to dissolve the dry powder composition and form a homogeneous solution, which is then extruded into the mixing head. The second aqueous solution can be simultaneously extruded into the mixing head. Finally, the resulting composition can then be extruded through the orifice onto a surface.

For example, the syringe barrels holding the dry powder and the basic solution may be part of a dual-syringe system, e.g., a double barrel syringe as described in U.S. Pat. No. 4,359,049, which is hereby incorporated by reference in its entirety. In this embodiment, the acid solution can be added to the syringe barrel that also holds the dry powder, so as to produce the homogeneous solution. In other words, the acid solution may be added (e.g., injected) into the syringe barrel holding the dry powder to thereby produce a homogeneous solution of the first and second components. This homogeneous solution can then be extruded into a mixing head, while the basic solution is simultaneously extruded into the mixing head. Within the mixing head, the homogeneous solution and the basic solution are mixed together to thereby form a reactive mixture. Thereafter, the reactive mixture is extruded through an orifice and onto a surface (e.g., tissue), where a film is formed, which can function as a sealant or a barrier, or the like. The reactive mixture begins forming a three-dimensional matrix immediately upon being formed by the mixing of the homogeneous solution and the basic solution in the mixing head. Accordingly, the reactive mixture is preferably extruded from the mixing head onto the tissue very quickly after it is formed so that the three-dimensional matrix forms on, and is able to adhere to, the tissue.

Figure 1B:
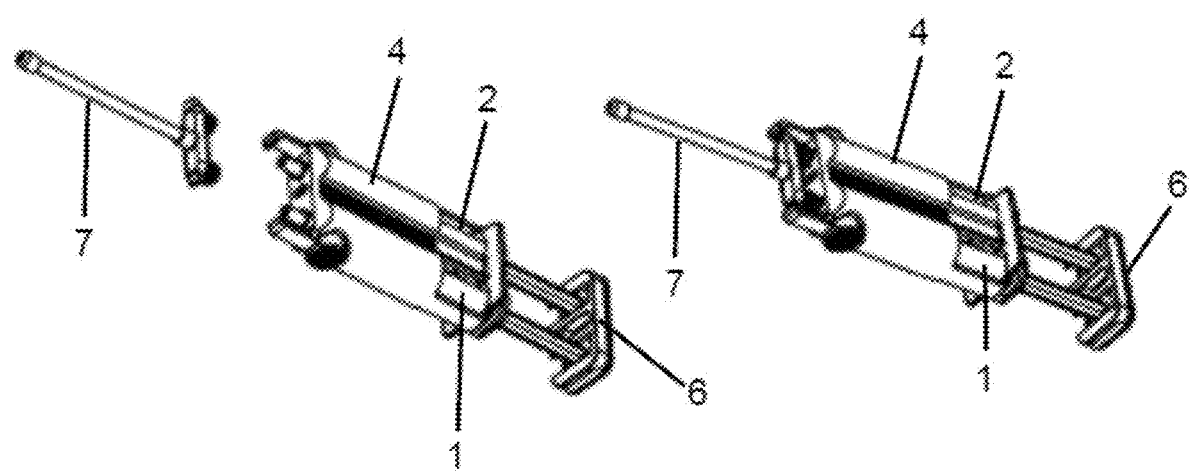
FIG. 1B shows the representative multi-compartment syringe device of FIG. 1A in further combination with an applicator for delivering the surgical sealant and adhesive composition to a site, for example, a biological tissue, where the composition is needed.

A preferred embodiment of a multi-compartment syringe system is shown in FIG. 1A. As shown, the device is comprised of three syringes, with first and second syringes 1, 2 of the multi-compartment syringe device 10 containing the two aqueous solutions and the third syringe 3 containing the dry powder composition. The two syringes 1, 2, containing the solutions are pre-assembled into a syringe housing 4 with a transfer port closure adapter 5 attached to the housing assembly 4 to allow mixing of the dry powder into the correct syringe. A syringe clip 6 can be uncoupled from one of the syringes and remain attached to the plunger rod of the syringe that does not require mixing with the dry powder composition, so as to facilitate separate, independent movement of a plunger (and thus the contents) of the first syringe 1. In this embodiment, the acid solution contained in the first syringe 1 is injected into the syringe barrel 3 holding the dry powder to thereby produce a homogeneous solution of the first, second, and third components. As shown in FIG. 1A, the syringe clip 6 can be coupled to both of the syringe plungers of the first and second syringes 1, 2, so as to facilitate substantially simultaneous flow of the homogeneous solution contained in the first syringe 1 and the basic solution contained in the second syringe 2 into a mixing head to thereby form a reactive mixture. The reactive mixture can then be delivered via an orifice onto a surface (e.g., tissue), where a film capable of functioning as a sealant, adhesive, barrier, or the like, can be formed. As shown in FIG. 1B, the empty third syringe 3 can be detached from the first syringe 1 and an applicator 7 attached onto the end of the syringe housing 4. Suitable delivery devices include the delivery devices currently used to deliver Coseal® surgical sealant compositions as shown in the packaging insert for this product.

Other systems for combining two reactive liquids are well known in the art, and include the systems described in U.S. Pat. Nos. 6,454,786, 6,461,325, 5,585,007, 5,116,315, and 4,631,055; and U.S. Patent Application Publication No. 2004/0068266, each of which is hereby incorporated by reference in its entirety.

Pressurized Delivery Devices: Other delivery systems for dispensing the multicomponent compositions disclosed herein may include pressurized delivery devices, examples of which are described in U.S. Patent Application Publication No. 2006/0071025, which is hereby incorporated by reference in its entirety. Such a pressurized delivery device may include a diffuser surface having an outlet extending therethrough that is positioned downstream from a plurality of inlets. While at least one inlet is adapted to communicate with a source of a pressurized carrier fluid, each of a plurality of inlets is adapted to communicate with a source of a different fluid component. Using this device, the dry powder solution is premixed with the first acidic aqueous solution to form a homogeneous solution as previously described and this solution is subsequently communicated as a first fluid component. The second alkaline aqueous buffer solution as described above is communicated as the second fluid component. Once the diffuser surface receives fluid components from the inlets, each received fluid component is pushed toward the outlet for mixing and dispensing therethrough by the pressurized carrier fluid, typically a gas such as air, from the carrier fluid inlet. The diffuser surface and the inlets may represent components of a mixing nozzle.

In general, there are two categories of gas enhanced nozzles for dispensing reactive components of a multicomponent composition—those that involve internal mixing and those that involve external mixing. When the diffuser surface is a part of a nozzle, the nozzle may be considered an internal-mixing nozzle. Unlike other internal-mixing technologies, the internal-mixing nozzle of the pressurized delivery device disclosed herein provides several features that serve individually and collectively to eliminate clogging. For example, a diffuser surface typically has a shape effective to direct and maintain each received fluid component in a different flow path on the diffuser surface toward the outlet for mixing therein and dispensing therethrough. Due to the minimal residence time of the mixture within the nozzle, reactive components do not have time to set and clog the nozzle before the mixture is forced out of the nozzle by the pressurized carrier fluid. In addition, the outlet may be aligned with any or all of the carrier fluid inlets that may be present in the nozzle to direct the pressurized carrier fluid in a manner that enhances fluid component mixing and to expel the mixture in a jet like manner. As the orientation of the diffuser surface relative to the inlets affects the performance of the device, the diffuser surface may be permanently affixed or immobilized with respect to the inlets; however, when the diffuser surface is detachable from the inlets, the nozzle may be disassembled to facilitate cleaning and/or replacement of parts. For example, the diffuser surface may be replaceable/and or disposable. Additionally, when the pressurized delivery device disclosed herein has a diffuser surface that is detachable from the inlets, the device may be constructed to allow assembly of the components in only configurations that align the diffuser surface to the inlets such that the performance of the device is optimized.

Kits

The compositions disclosed herein can be packaged in kits and used in a variety of medical applications. The kit would include aqueous solutions, as well as written or otherwise illustrated instructions for use. A typical kit for use in medical applications, comprises: (a) a homogeneous dry powder composition comprised of: (i) a first component having a polymer core substituted with at least two sulfhydryl groups, (ii) a second component having a polymer core substituted with at least two sulfhydryl-reactive groups, and (iii) a third component comprising a polymer core substituted with at least one L-3,4-dihydroxyphenylalanine (L-DOPA) group and at least one sulfhydryl-reactive group; (b) a first aqueous solution having a pH of about 1 to 5.5; and (c) a second aqueous solution having a pH of about 6 to 11; wherein each component is packaged separately and admixed immediately prior to use. As is evident to those of ordinary skill in the art, prior to use, each component should be packaged separately such that the component remains sterile and does not contact another component. As an example, two of the individual components can be packaged in separate sterile packages such as separate syringe barrels of a multiple-compartment syringe system having multiple syringe barrels as described above.

In another embodiment, the kit further comprises a delivery system that will allow the surgical sealant and/or adhesive composition to be delivered as a spray. The spray can be generated by manually mixing the components and passing them through a spray nozzle. The spray generation can also be accomplished by using a flow of gas (for example, air, nitrogen, carbon dioxide). Suitable delivery devices that may be included in the kits include the multi-compartment syringe device and/or the pressurized delivery devices described herein.

In one embodiment of the kit, a multi-compartment device is included in the kit. As previously described, the multi-compartment device may be a multiple-compartment syringe device having multiple barrels, a mixing head, and an exit orifice, wherein the dry powder composition, the first aqueous solution, and the second aqueous solution are housed separately in the multiple-compartment syringe device.

In another embodiment of the kit, a pressurized delivery device is included in the kit. As previously described, the pressurized delivery device includes a plurality of fluid component inlets each adapted to communicate with a source of different fluid components; at least one carrier fluid inlet adapted to communicate with a source of a pressurized carrier fluid; a diffuser surface located downstream from the plurality of fluid component inlets and the at least one carrier fluid inlet; and an outlet extending through the diffuser surface, wherein the diffuser surface is adapted to receive fluid components thereon and has a shape effective to direct and maintain each received fluid component in a different flow path toward the outlet for mixing and dispensing therethrough by the pressurized carrier fluid from the at least one carrier fluid inlet.

Suitable kits are not limited to the devices described herein and may also include any other suitable delivery device known in the art of drug delivery.

Uses

The surgical sealant and adhesive compositions disclosed herein can be used in a variety of different applications. In general, these compositions can be adapted for use in any tissue engineering application where synthetic gel matrices are currently being utilized. For example, the compositions are useful as tissue sealants and adhesives, vascular sealants, in tissue augmentation, in tissue repair, as hemostatic agents, and in preventing tissue adhesions, and may be used in a variety of open, endoscopic, and laparoscopic surgical procedures. One of skill in the art can easily determine the appropriate administration protocol to use with any particular composition having a known gel strength and gelation time.

In one application, the compositions described herein can be used for medical conditions that require a coating or sealing layer to prevent the leakage of gases, liquid or solids.

Methods of use typically entail applying the composition to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or urethra to stop or minimize the leakage of urine; 5) dura to stop or minimize the leakage of cerebrospinal fluid; and/or 6) skin or serosal tissue to stop the leakage of serosal fluid. These compositions may also be used to adhere tissues together such as small vessels, nerves or dermal tissue. The compositions can be used 1) by applying them to the surface of one tissue and then a second tissue may be rapidly pressed against the first tissue or 2) by bringing the tissues in close juxtaposition and then applying the compositions such that both the first and second tissue are contacted with the compositions. In addition, the compositions can be used to fill spaces in soft and hard tissues that are created by disease or surgery.

Therefore, one embodiment is a method of sealing tissue of a patient comprising the steps of: (a) providing (i) a first component having a polymeric core substituted with nucleophilic groups (e.g., amino groups or thiol groups), a second component having a polymeric core substituted with electrophilic groups (e.g., succinimidyl groups), and (iii) a third component comprising a polymer core substituted with at least one L-3,4-dihydroxyphenylalanine (L-DOPA) group and at least one electrophilic group (e.g., a succinimidyl group); (b) rendering the nucleophilic and electrophilic groups reactive by exposing the first component, second component, and third component to an aqueous environment having a pH sufficient to effect reaction; and (c) placing the mixture into contact with tissue and allowing a three-dimensional matrix to form and seal the tissue.

In another embodiment, the surgical adhesive and/or sealant compositions can be applied in conjunction with an implanted medical device such that it prevents the leakage of gases, liquids or solids from the device or from the device-tissue interface. For example, following the implantation of a vascular graft (either synthetic or biological), there is often leakage of blood through the suture holes in the graft or at the interface between the graft and the tissue. The surgical adhesive and/or sealant composition disclosed herein can be applied to this area to prevent further blood leakage.

In an embodiment, a method of sealing tissue of a patient comprises: (a) dissolving a dry powder composition comprising (i) a first component having a polymer core substituted with at least two sulfhydryl groups, (ii) a second component having a polymer core substituted with at least two sulfhydryl-reactive groups, and (iii) a third component comprising a polymer core substituted with at least one L-3,4-dihydroxyphenylalanine (L-DOPA) group and at least one sulfhydryl-reactive group in a first aqueous solution having a pH of about 1 to about 5.5 to form a homogeneous solution; (b) adding a second aqueous solution having a pH of about 6 to about 11 to the homogeneous solution to form a mixture; and (c) placing the mixture into contact with a tissue surface and allowing a three-dimensional composition to form on the tissue surface.

EXAMPLES

Example 1

Synthesis of L-DOPA- and Succinimidyl-Terminated PEG

An L-DOPA- and succinimidyl-terminated PEG (PEG-NHS-DOPA) was prepared according to the following procedure. To prepare protected L-DOPA, about 1.15 g (3 mmol) of borax decahydrate was dissolved into 30 mL of distilled water in a dual-necked round-bottom flask. The flask was put under inert atmosphere and about 0.20 g (1 mmol) of L-DOPA was added. The solution was then stirred at room temperature for 30 minutes and the pH was maintained with about 0.3 g (2.8 mmol) of sodium carbonate. The measured pH was 8-9.

To prepare PEG-NHS-DOPA, about 5.5 g (0.50 mmol) of pentaerythritol polyethylene glycol ether tetra-succinimidyl glutarate, $M_w$=11 kDa (PEG-NETS) in 15 mL acetone was added to the mixture containing L-DOPA. After stirring overnight while protected from sunlight, the solution was acidified to pH 2 with concentrated hydrochloride acid.

In a specific example, PEG-NHS-DOPA was prepared according to the procedure described above using 1.22 g (3.20 mmol) borax, 0.23 g (1.16 mmol) L-DOPA, 0.3 g sodium carbonate, and 5.6 g (0.51 mmol) PEG-NETS. The molar ratio of succinimidyl groups to L-DOPA is 1.7.

The PEG-NHS-DOPA was purified by extracting three times with 10 mL dichloromethane. The organic phases were combined and dried with sodium sulfate. An Arnow's test was performed on the aqueous and the dichloromethane phases as described in Example 2. The solvent was then evaporated under a flux of nitrogen until a syrupy liquid remained. The liquid was poured into a petri dish and the product left to dry under $N_2$ flow. Once a soggy powder was obtained, the product was poured in a tube and drying under $N_2$ flow was continued. The dry powder obtained was put in a tube and stored in the freezer.

Example 2

Arnow Test

The Arnow test is a colorimetric test for characterization of catechol functional groups. The Arnow test was used to characterize the relative distribution of L-DOPA in the aqueous and organic phases from the purification of the PEG-NHS-DOPA in Example 1.

A solution of molybdic acid/nitrite (Mo/$NO_2$) was prepared by adding 2 g of molybdic acid sodium salt dihydrate and 2 g of sodium nitrite to a 100 mL beaker and dissolving the solids in 20 mL of distilled water.

A control solution containing L-DOPA at 1% of the initial concentration used for the reaction in Example 1 was prepared by dissolving 0.05 g (0.25 mmol) of L-DOPA in 100 mL of water in a beaker. 1 mL of the solution was removed and diluted with 5.6 mL of distilled water to give a final concentration of 0.38 mM.

A drop of the aqueous phase and organic phase from Example 1 and of the control solution was poured into separate tubes. To each tube was added 1 M HCl and the tubes were shaken until the solutions were homogeneous. Next, 1 mL of the molybdic acid/nitrite solution was added. Then, an excess of 1M NaOH was added.

In presence of a catechol functional group, the solution turns bright yellow after addition of the molybdic acid/nitrite solution and red after addition of an excess of 1M NaOH.

The blank tube (no sample solution) remained colorless during all steps. The DOPA control contained too low of a DOPA concentration to give a visible response, and remained colorless in the presence of the molybdate/nitrate solution and did not turn red in presence of the NaOH solution. The organic phase demonstrated a strong bright yellow color in the presence of the molybdate/nitrate solution, which turned to deep red in the presence of excess NaOH. The aqueous phase demonstrated a light yellow color in the presence of the molybdate/nitrate solution and a pale red color in the presence of excess NaOH. These results demonstrated that a major portion of the L-DOPA was extracted with the PEG into the organic phase.

Example 3

NHS Bonding Test

The presence and activity of the succinimidyl group of the PEG-NHS-DOPA of Example 1 was assessed according to the following procedure. To a test tube was added 0.3 g PEG-NHS-DOPA and 0.3 g 4-arm, thiol-terminated PEG (PEG-SH) (1:1 weight ratio of PEG-NHS-DOPA to PEG-SH). A control sample was prepared using 0.3 g PEG-NHS-DOPA only. Both samples were then dissolved in 1 mL dilute HCl solution. Next, 1 mL of phosphate/carbonate buffer was added in the tubes to raise the pH to 8-9, after which the mixtures were homogenized and allowed to react for 10 minutes. A hydrogel was not observed after 10 minutes.

A solution of sodium periodate was prepared to crosslink DOPA groups. The solution was prepared by dissolving 0.1 g sodium periodate in 5 mL phosphate buffer. A few drops of the sodium periodate solution was added to both samples. Within a few seconds, a hydrogel formed in the PEG-NHS-DOPA/PEG-SH sample, but not in the control sample, thereby evidencing crosslinking and formation of a three-dimensional product suitable for use as a surgical adhesive and/or sealant.

Example 4

Adhesion to Liver Tissue

A PEG-NHS-DOPA-containing surgical adhesive was prepared using a Coseal Surgical Sealant (Coseal) kit composed of two synthetic polyethylene glycols (PEGs) as a powder, a dilute hydrogen chloride solution and a sodium phosphate/sodium carbonate solution. To prepare the PEG-NHS-DOPA-containing component, the plunger was removed from the powder syringe of the Coseal kit (i.e., the syringe containing the two synthetic PEGs). PEG-NHS-DOPA was weighed and added to the PEG powder, and the plunger was reinserted. For the adhesion experiments described below, the mass of PEG-NHS-DOPA was 0.36 g corresponding to a molar quantity of $33 \times 10^{-3}$ mmol DOPA (assuming one DOPA substitution per 11 kD PEG macromolecule). The Coseal kits were then prepared as described in their instructions for use.

To assess adhesion of the PEG-NHS-DOPA-containing surgical adhesive on a wet surface, the Coseal sealant with added PEG-NHS-DOPA (referred to as Coseal DOPA (+)) and unmodified Coseal (referred to as Coseal DOPA (−)) were applied to dry and wet areas of a slice of beef liver. The slice of liver was set on the bench and an area was defined for application of Coseal DOPA (+) and Coseal DOPA (−) onto wet and dry surfaces in a 2×2 matrix as shown in FIG. 2.

Figure 2:
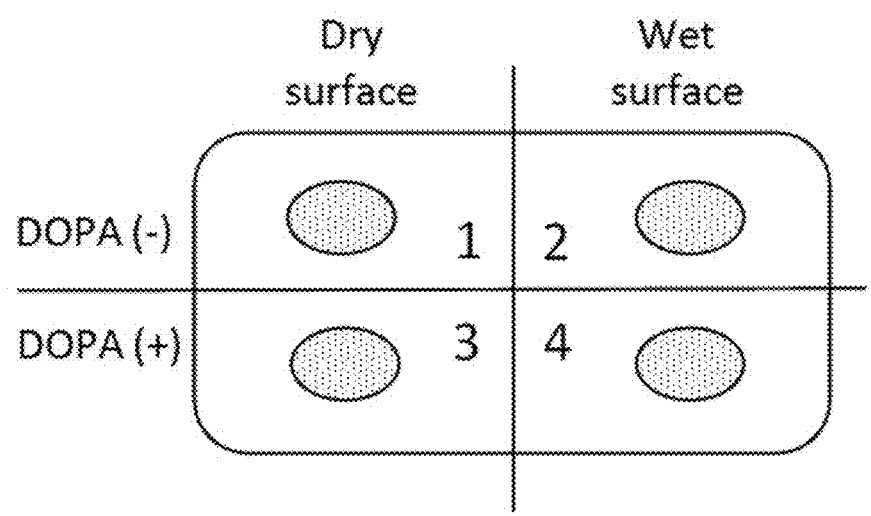
FIG. 2 is a schematic drawing showing the 2×2 matrix defined for application of Coseal® surgical sealant (Baxter International) with DOPA ("Coseal DOPA (+)") and Coseal® surgical sealant without DOPA ("Coseal DOPA (−)") onto wet and dry surfaces.

Half of the area (quadrants 2 and 4, as shown in FIG. 2) were wetted with distilled water while avoiding contamination of the dry areas (quadrants 1 and 3, as shown in FIG. 2). Excess water was removed by hanging the slice of liver vertically for a few seconds. Equal volumes of Coseal DOPA (+) and (−) were then applied onto the wet and the dry areas of the slice of liver. The applied adhesives were allowed to polymerize for a minimum of 5 minutes.

Figure 3A:
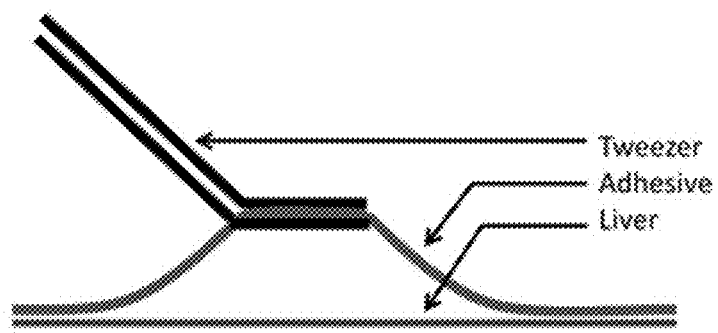
FIG. 3A is a schematic drawing of an adhesive layer demonstrating poor adhesion to a liver surface.
Figure 3B:
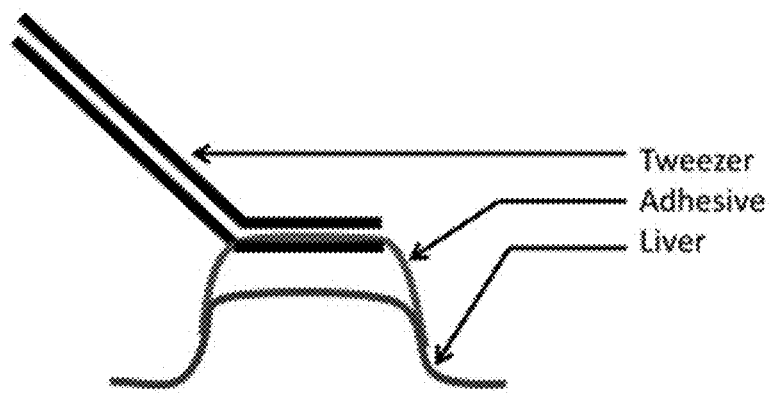
FIG. 3B is a schematic drawing of an adhesive layer demonstrating strong adhesion to a liver surface.

The adhesiveness of Coseal DOPA (+) and (−) under dry and wet conditions was assessed by using tweezers to peel off and lift up the polymerized adhesive layer. The tweezers were gently introduced between the liver and the adhesive layer and lifted to assess the adhesiveness of the adhesive layer on the liver surface as shown in FIGS. 3A and 3B.

The results of the adhesiveness assessment are shown in FIG. 4A (Coseal DOPA (−) applied on dry surface), FIG. 4B (Coseal DOPA (+) applied on dry surface), FIG. 4C (Coseal DOPA (−) applied on wet surface), and FIG. 4D (Coseal DOPA (+) applied on wet surface).

As shown in FIG. 4A, Coseal DOPA (−) demonstrated adhesion to a dry surface, with the adhesive material pulling the surface of the liver. As shown in FIG. 4B, the adhesiveness with Coseal DOPA (+) was relatively stronger, with the adhesive bond being able to support (i.e., lift) the piece of liver in dry conditions. As shown in FIG. 4C, Coseal DOPA (−) demonstrated slight adhesion to a wet surface. As shown in FIG. 4D, Coseal DOPA (+) demonstrated adhesion to the wet surface, but was torn during the test demonstrating reduced cohesive strength. Without wishing to be bound by theory, it is believed that the reduced cohesive strength may be due to reduced crosslinking density in the presence of PEG-NHS-DOPA due to the DOPA groups not being capable of crosslinking. It is theorized that crosslinking density can be enhanced by oxidation of DOPA groups.

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

What is claimed is:

1. A compound comprising a polymer core substituted with at least one L-3,4-dihydroxyphenylalanine (L-DOPA) group and at least one sulfhydryl-reactive group, wherein the polymer core is branched poly(ethylene oxide), and wherein the sulfhydryl-reactive group is a succinimidyl group, an acrylate group, or a vinyl sulfone group.

2. The compound of claim 1, wherein the polymer core is a 4-arm poly(ethylene oxide), a 6-arm poly(ethylene oxide), or an 8-arm poly(ethylene oxide).

3. The compound of claim 1, wherein the compound has a structure of Formula I:

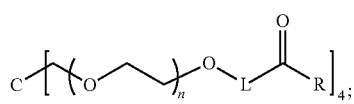

(I)

wherein:
each R is independently a sulfhydryl-reactive group or

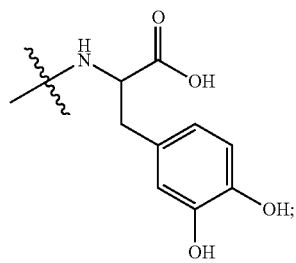 [SMILES: *NC(Cc1ccc(O)c(O)c1)C(=O)O]

L is null, —(CH$_2$)$_{1-5}$—, —CO(CH$_2$)$_{1-5}$—, —NHCO(CH$_2$)$_{1-5}$—, —(CH$_2$)$_{1-5}$NHCO(CH$_2$)$_{1-5}$—; and
each n is independently 15 to 150;
provided that at least one R group is

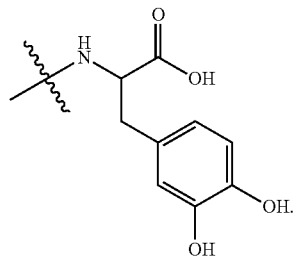 [SMILES: *NC(Cc1ccc(O)c(O)c1)C(=O)O]

4. The compound of claim 3, wherein L is —CO(CH$_2$)$_3$— or —NHCO(CH$_2$)$_2$—.

5. The compound of claim 3, wherein the sulfhydryl-reactive group is

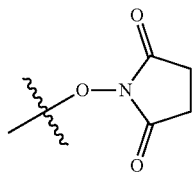

6. The compound of claim 1, wherein the compound has a structure of Formula II or Formula III:

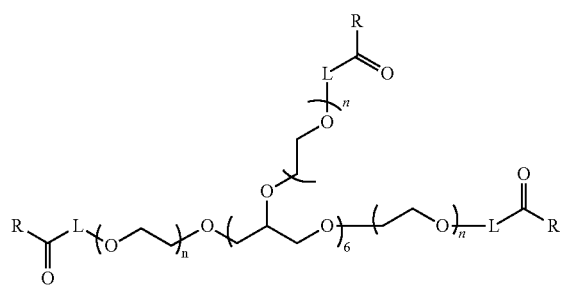

(II)

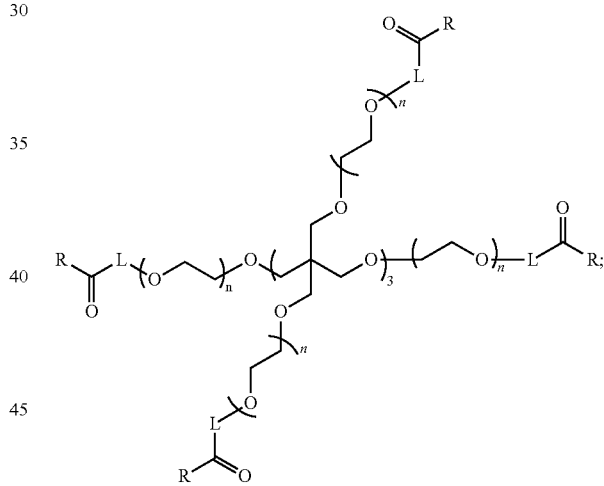

(III)

wherein:
each R is independently a sulfhydryl-reactive group or

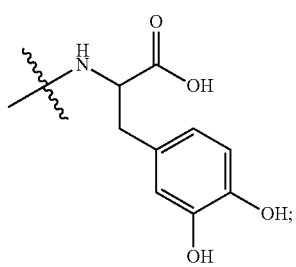 [SMILES: *NC(Cc1ccc(O)c(O)c1)C(=O)O]

L is null, —(CH$_2$)$_{1-5}$—, —CO(CH$_2$)$_{1-5}$—, —NHCO(CH$_2$)$_{1-5}$—, or —(CH$_2$)$_{1-5}$NHCO(CH$_2$)$_{1-5}$—; and
each n is independently 15 to 150;

provided that at least one R group is

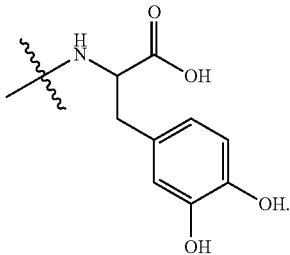 [SMILES: *NC(Cc1ccc(O)c(O)c1)C(=O)O]

7. The compound of claim 6, wherein L is —CO(CH₂)₂—, —CO(CH₂)₃—, or —(CH₂)₂NHCO(CH₂)₂—.

8. The compound of claim 1, wherein the sulfhydryl-reactive group is

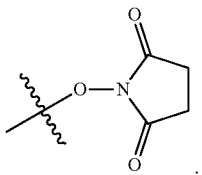 [SMILES: *ON1C(=O)CCC1=O]

9. A dry powder composition comprising (i) a component having a polymer core substituted with at least two sulfhydryl groups and (ii) the compound of claim 1.

10. The dry powder composition of claim 9, further comprising a component having a polymer core substituted with at least two sulfhydryl-reactive groups.

11. A solution composition comprising (i) a component having a polymer core substituted with at least two sulfhydryl groups and (ii) the compound of claim 1, wherein the solution has a pH of about 1 to about 5.5.

12. The solution composition of claim 11, further comprising a component having a polymer core substituted with at least two sulfhydryl-reactive group.

13. A kit comprising:
(a) a dry powder composition comprising a first component having a polymer core substituted with at least two sulfhydryl groups, a second component having a polymer core substituted with at least two sulfhydryl-reactive groups, and a third component comprising a polymer core substituted with at least one L-3,4-dihydroxyphenylalanine (L-DOPA) group and at least one sulfhydryl-reactive group;
(b) a first aqueous solution having a pH of about 1 to about 5.5; and
(c) a second aqueous solution having a pH of about 6 to about 11;
wherein each of (a), (b), and (c) is packaged separately prior to use.

14. The kit of claim 13, wherein the first component polymer core, second component polymer core, and third component polymer core are all branched poly(ethylene oxide).

15. The kit of claim 13, wherein the first component polymer core, second component polymer core, and third component polymer core are independently 4-arm poly(ethylene oxide) and/or 8-arm poly(ethylene oxide).

16. The kit of claim 13, wherein the first component comprises a 4-arm, thiol-terminated poly(ethylene oxide) and the second component comprises a 4-arm, succinimidyl-terminated poly(ethylene oxide).

17. The kit of claim 13, wherein the first component is

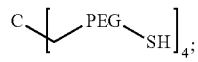

wherein PEG is poly(ethylene oxide).

18. The kit of claim 13, wherein the second component is

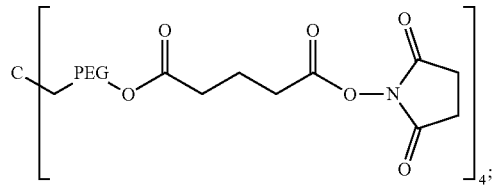

wherein PEG is poly(ethylene oxide).

19. The kit of claim 13, further comprising a delivery device.

20. The kit of claim 19, wherein the delivery device is a multi-compartment syringe device or a pressurized delivery device.

21. A composition prepared by reacting a component having a polymer core substituted with at least two sulfhydryl groups with (i) a component having a polymer core substituted with at least two sulfhydryl-reactive groups and (ii) the compound of claim 1.

22. A compound has a structure of Formula II or Formula III:

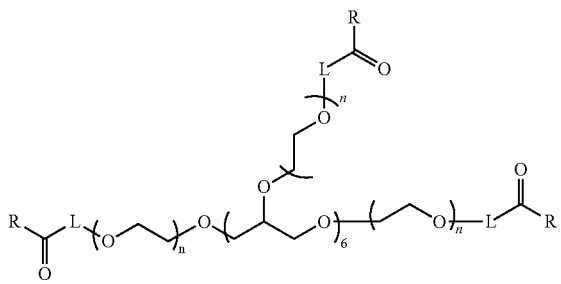

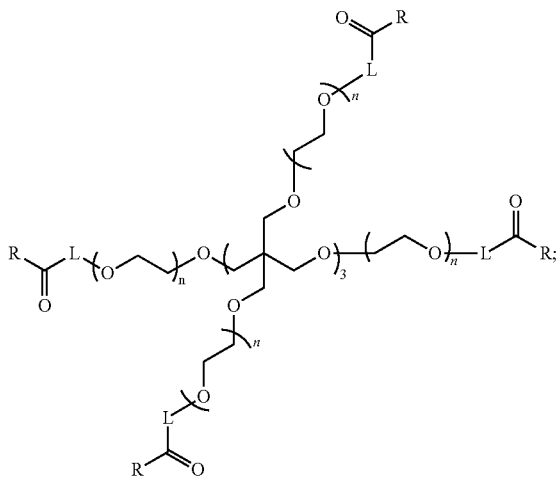

wherein:
each R is independently a sulfhydryl-reactive group or
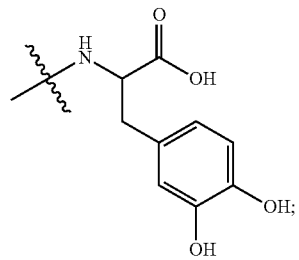 [SMILES: *NC(Cc1ccc(O)c(O)c1)C(=O)O]
L is null, —(CH$_2$)$_{15}$—, —CO(CH$_2$)$_{1-5}$—, —NHCO(CH$_2$)$_{1-5}$—, or —(CH$_2$)$_{1-5}$NHCO(CH$_2$)$_{1-5}$—; and
each n is independently 15 to 150;
provided that at least one R group is wherein the sulfhydryl-reactive group is
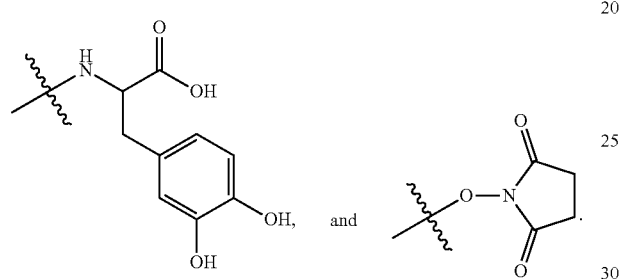
\* \* \* \* \*